United States Patent [19]

Cosgrove

[11] Patent Number: 5,053,534

[45] Date of Patent: Oct. 1, 1991

[54] PROCESS FOR MAKING A DICARBOXYLIC ACID

[75] Inventor: John P. Cosgrove, Charleston, S.C.

[73] Assignee: Westvaco Corporation, New York, N.Y.

[21] Appl. No.: 596,021

[22] Filed: Oct. 11, 1990

[51] Int. Cl.$^5$ ............................................... C07C 51/00
[52] U.S. Cl. ..................................... 562/509; 560/127
[58] Field of Search ........................ 562/509; 560/127

[56] References Cited

U.S. PATENT DOCUMENTS

| | | | |
|---|---|---|---|
| 2,343,644 | 3/1944 | Cawley | 260/405.6 |
| 3,162,658 | 12/1964 | Baltes et al. | 260/405.6 |
| 3,753,968 | 8/1973 | Ward | 560/190 |
| 4,156,095 | 5/1979 | Jevne et al. | 562/509 |

OTHER PUBLICATIONS

J. P. Cowan, "The Journal of the American Oil Chemicals Society", vol. 31, 11/54, pp. 529–535.
B. J. Ward et al., "The Journal of the American Oil Chemicals Society", vol. 52, 7/75, pp. 219–224.
"Westvaco Diacid® 1550 and 1595 Dicarboxylic Acids", Westvaco Chemical Division Product Data Bulletin, May, 1990.

*Primary Examiner*—Jose G. Dees
*Assistant Examiner*—Vera C. Clarke
*Attorney, Agent, or Firm*—Daniel B. Reece, IV; Terry B. McDaniel; R. L. Schmalz

[57] ABSTRACT

A 21-carbon aliphatic branched chain dicarboxylic acid is produced by reacting pre-conjugated fatty acid (which contains linoleic acid) with acrylic acid at a temperature between 180° C. and 300° C. No catalyst or solvent is necessary for the reaction to occur. The reaction product is subsequently distilled to yield high purity dicarboxylic acid.

5 Claims, No Drawings

PROCESS FOR MAKING A DICARBOXYLIC ACID

FIELD OF THE INVENTION

This invention relates to the production of a dicarboxylic acid having 21 carbon atoms. In particular, this invention relates to a novel process for making a high purity dicarboxylic acid having 21 carbon atoms from conjugated linoleic acid.

BACKGROUND OF THE INVENTION

Several applications have been developed for derivatives of dicarboxylic acid in the fields of coatings, detergents, and corrosion inhibitors. As used herein the term "dicarboxylic acid" is intended to mean a dicarboxylic acid having 21 carbon atoms, but in some instances includes minor amounts of dicarboxylic acid of other molecular weights. The versatility these materials exhibit in meeting the requirements of a variety of product applications is evidenced by their widespread use in commerce.

It is known in the art to react conjugated linoleic acid with certain dienophiles or activated mono-olefins to produce various polyfunctional Diels-Alder adducts. It is also known that the reactivity of the conjugated linoleic acid is determined by its geometrical isomerism about the double-bond system; and that the preferred reactive isomer has a trans-trans configuration. As demonstrated by the article, "Polymerization, Copolymerization, and Isomerization", J. C. Cowan, *The Journal of the American Oil Chemicals Society*, Vol. Nov. 31, 1954, pp. 529-535, it has long been taught that the use of catalysts (such as iodine, sodium or potassium bisulfates, sulfur, selenium, noble metals, and the like) to isomerize the cis-trans isomers into the trans-trans state is necessary to induce these cis-trans isomers of conjugated linoleic acid to react in a Diels-Alder reaction.

The method preferred by industry for the production of dicarboxyic acid is taught in commonly assigned U.S. Pat. No. 3,753,968, which is hereby incorporated by reference. There, a fatty acid mixture containing both conjugated and non-conjugated linoleic acid is simultaneously reacted with acrylic acid in the presence of an iodine catalyst to produce a fatty acid mixture containing dicarboxylic acid. This mixture is subsequently distilled to recover a linoleic free fatty acid fraction and a dicarboxylic acid fraction.

At the time this process was patented, it was believed that the amount of dicarboxylic acid formed was approximately the same as the starting content of linoleic acid in the fatty acid mixture. In other words, that the dicarboxylic acid material left after distillation was about 92% pure dicarboxylic acid. However, subsequent improvements in analytical instrumentation and techniques came to show that about 10% of what had been believed to be dicarboxylic acid was, in actuality, a C-21 lactone. This lactone was formed by the cyclization of the secondary carboxylic acid with the double bond of the cyclohexene ring. The lactonization reaction can result from the interaction of iodine with the double bond at the temperatures employed in the dicarboxylic acid synthesis.

It is difficult to remove the C-21 lactone from the dicarboxylic acid due to their structural similarity. Repeated wiped-film distillations will remove the lactone, but the procedure is costly and the final yield of purified dicarboxylic acid is extremely low.

It is also possible to purify the crude dicarboxylic acid by distillation of its methyl or dimethyl ester, as taught in U.S. Pat. No. 3,753,968. However, this procedure has proven too difficult and expensive to be feasible at a commercial scale.

Thus, no commercially feasible process has previously emerged which would produce a dicarboxylic acid of higher purity than that obtained via the method taught in U.S. Pat. No. 3,753,968 —a purity of only 85%. As a consequence, the potential applications for dicarboxylic acid in the fields of lubricants, coatings, detergents, plasticizers, and corrosion inhibitors have always been limited by the presence of other substances in the reaction mixture.

Although the most extensive uses of dibasic acids are to be found in producing polymers, dicarboxylic acid (as currently produced) has little or no utility in this area. It is recognized that one needs a high percentage of chain-forming difunctional molecules in order to be able to make a high molecular weight polymer. As 15% of the current dicarboxylic acid mixture is monofunctional or trifunctional material, it is far too impure to be used in polymer production.

Therefore, it is the object of this invention to provide an economical process for producing a dicarboxylic acid of high purity. Other objects, features, and advantages will be evident from the following disclosure.

SUMMARY OF THE INVENTION

The object of this invention is met by reacting pre-conjugated fatty acid (which contains linoleic acid) with acrylic acid at elevated temperatures. No catalyst or solvent is necessary for the reaction to occur. The reaction product is subsequently distilled to yield a high purity dicarboxylic acid.

As noted above, it is taught in the art that this Diels-Alder reaction needs a catalyst to isomerize the cis-trans isomers into the reactive trans-trans configuration. If a catalyst is not added, it is taught that the reaction will be limited to the reactive trans-trans isomers.

Therefore, it was unexpected that the reaction temperature employed in this novel process was high enough to thermally isomerize the cis-trans linoleic acid into the trans-trans form. This permitted conversion of almost 100% of the pre-conjugated linoleic acid to occur without a catalyst being present (and, therefore, without forming C-21 lactone). This results in a higher yield of more easily purified dicarboxylic acid than that derived from the use of unconjugated fatty acid and any catalyst, including iodine.

Aside from the obvious economic benefits that accrue from being able to omit the catalyst, research has shown that the dicarboxylic acid produced by this process is thermally stable and does not undergo any side reactions (in the absence of a catalyst) at the reaction temperature. This stability facilitates distillation to higher purity levels

DESCRIPTION OF THE PREFERRED EMBODIMENT

The novel process that yields a high purity dicarboxylic acid reacts acrylic acid with a pre-conjugated fatty acid (which contains linoleic acid) at an elevated temperature. The product of the reaction then is distilled to yield a dicarboxylic acid substantially free of impurities.

Suitable fatty acids must include linoleic acid, and must be capable of pre-conjugation. Included in this list of fatty acids are: tall oil, safflower oil, corn oil, peanut oil, linseed oil, soya, and cottonseed. This list is intended to be representative and it will be obvious to those skilled in the art that a variety of other sources of fatty acids can be used.

It is also recognized in the art that several processes are known for conjugating various fatty acids, as shown in U. S. Pat. No. 2,343,644 and U.S. Pat. No. 3,162,658, which are hereby incorporated by reference. The method chosen to pre-conjugate the fatty acid will depend upon cost considerations, the type of fatty acid to be conjugated, the desired conversion, and other factors.

The acrylic acid is added to the pre-conjugated fatty acid in an amount up to about 26% by weight of the fatty acid. While adding the acrylic acid at the beginning of the reaction gave good results, it is preferred to meter the acrylic acid addition over a period of at least two hours.

The reaction to produce dicarboxylic acid is conducted at a temperature between 180° C. and 300° C. The preferred temperature for the reaction is around 230° C. to 260° C. for a period of between two to four hours. At the end of the reaction, the reaction mixture consists of dicarboxylic acid, unreacted fatty acid, and a C-thermal dimer. This reaction mixture is subjected to a two-stage distillation wherein the first distillation serves to remove the monomer from the mixture, while the second distillation removes the dimer; thus leaving a substantially pure dicarboxylic acid. While several viable methods of distillation are known, the preferred method utilizes fractional column distillation as the first step, followed by distillation on a wiped-film evaporator. An analysis of the resulting dicarboxylic acid typically made via this method is shown in Table I below.

TABLE I

| Analysis of Dicarboxylic Acid | |
|---|---|
| Fatty and Resin Acids | 3% maximum |
| 21-carbon dibasic acids | 97% minimum |
| Internal lactone | none detected |
| 36-carbon dimeric acids | none detected |
| Garden Color | 4 maximum |
| Acid Number | 308-318 |
| Saponification Number | 312-318 |

The theoretical acid number and saponification number of a 21-carbon dibasic acid is 318. The fatty and resin acids percentages are for all materials which elute before the first diacid isomer on a non-polar gas chromatogragh (GC) column.

The following examples are provided to further illustrate the present invention and are not to be construed as limiting the invention in any manner.

EXAMPLE 1

To a 1L Parr reactor equipped with a stirrer was charged 500 g of PAMOLYN®380 fatty acid. (PAMOLYN®380 is a tall oil derived fatty acid containing 69% conjugated linoleic acid, sold by Hercules Incorporated.) The fatty acid was heated, with stirring, to a final temperature of 240° C. When the temperature of the Parr reactor reached 180° C., the addition of 130 g of acrylic acid was begun. The acrylic acid was pumped into the Parr reactor via a Milton Roy pump at the rate of 92 ml per hour, until all 130 g of acrylic acid had been added. Once the top temperature of 240° C. was obtained, the reaction was maintained at this temperature for four hours, generating a maximum pressure of 70 psi. At the end of the reaction, the reaction mixture consisted of 5-10% C-36 thermal dimer, 25% unreacted fatty acid (primarily oleic), and 60-65% dicarboxylic acid.

The resultant dicarboxylic acid reaction mixture was purified on a two-inch Pope wiped-film evaporator (WFE). The first pass, at 200° C., served to remove the monomer from the product, resulting in a material that was about 75% dicarboxylic acid. The crude dicarboxylic acid was rerun on the WFE at a temperature of 290° C., taking the dicarboxylic acid as a heads cut and leaving the dimer and any polymerized acrylic in the bottoms. This second and final pass resulted in a product that was at least 95% dicarboxylic acid with a 53% overall yield.

EXAMPLE 2

A series of reactions were run where the method of acrylic acid addition, the top reaction temperatures, and the reaction times were varied.

Eight reactions were run where an amount of 500 g of PAMOLYN® 380 fatty acid was charged into a IL Parr reactor equipped with a stirrer. To runs 1-4, an amount of 125 g of acrylic acid was added to the fatty acid at the beginning of the reaction. These runs were heated, with stirring, to different combinations of top reaction temperatures and lengths of time. To runs 5-8, a total of 125 g of acrylic acid was metered into the reaction, with stirring, over a two hour period starting when the reactor reached 180° C. These runs were also heated, with stirring, to different combinations of top reaction temperatures and lengths of time. The results are listed in Table II below.

TABLE II

| RUN # | ACRYLIC ACID ADDITION | TOP REACTION TEMPERATURE | TIME OF REACTION | % YIELD OF DICARBOXYLIC ACID |
|---|---|---|---|---|
| 1 | At beginning | 250° C. | 2 hrs | 52 |
| 2 | " | 250° C. | 3 hrs | 57 |
| 3 | " | 230° C. | 2 hrs | 47 |
| 4 | " | 230° C. | 3 hrs | 49 |
| 5 | Metered | 230° C. | 2 hrs | 51 |
| 6 | " | 230° C. | 3 hrs | 58 |
| 7 | " | 250° C. | 2 hrs | 58 |
| 8 | " | 250° C. | 3 hrs | 66 |

As shown above, the better yields of dicarboxylic acid are produced when the acrylic acid addition is metered over a period of at least two hours. Also, higher reaction temperatures and longer reaction times led to better dicarboxylic acid yields.

EXAMPLE 3

A 50 gallon reactor was charged with 66.481 kilograms of PAMOLYN® 380 (79.8% by weight) and 17 grams of 4-methoxyphenol (MEHQ, 0.1% based on acrylic acid). The reactor was closed and heated to 250° C., with stirring. When the reactor temperature had reached 170° C. the addition of 16.767 kilograms (20.1% by weight) of acrylic acid was begun. The acrylic acid was added to the reactor by pumping it through the nitrogen sparge line below the level of the fatty acid. The pump, a 2.1 gph metering pump, was run at 100% stroke. The reactor was allowed to continue heating to 250° C. while the acrylic acid was added.

The reaction was continued for two hours after all the acrylic acid had been added. The maximum pressure generated was 50 psi, at 250° C., at the end of the addition. The reaction product comprised 65% dicarboxylic acid according to GC analysis. The reactor was cooled to 200° C., and the pressure carefully vented into a caustic trap. The reaction mixture was held at 200° C. and sparged with nitrogen for one to two hours, until all the unreacted acrylic acid had been sparged out of the reactor.

The sparged reaction mixture was distilled on an Oldershaw column which contained 14 elements of Sulzer BX packing. The bottoms product was distilled further on a Pfaulder wiped-film evaporator. The final, overall yield of dicarboxylic acid was 55.1%. This dicarboxylic acid had a final acid number of 317, and a final residual fatty acid content of 1%.

EXAMPLE 4

Two reactions were run where the percent by weight of the acrylic acid, based on the weight of fatty acid, was varied.

Each of two 1 L Parr reactors (equipped with stirrers) were charged separately with 600 g of conjugated L-1 fatty acid. (L-1 is a tall oil derived fatty acid containing roughly equivalent amounts of oleic and linoleic acid, and less that 1% resin acid, made by Westvaco). The fatty acid was heated, with stirring, to a final temperature of 250° C. When the temperatures of the Parr reactors reached 180° C., the two respective additions of acrylic acid were begun. The respective amounts of acrylic acid were pumped into the Parr reactors via Milton Roy pumps at the rate of 92 ml per hour, until all the acrylic acid had been added. The top temperature of 250° C. was maintained for four hours, generating a maximum of 70 psi. The results are listed in Table III below.

TABLE III

| Run # | Amount Acrylic Acid* | Dicarboxylic Acid Yield** |
|---|---|---|
| 1 | 12.5% | 40% |
| 2 | 15.0 | 37 |

*Weight percent acrylic acid, based on weight of fatty acid.
**Yields are based on gas chromatography.

The dicarboxylic acid purification was done on a two-inch glass, laboratory WFE. The first pass was at 210° to 220° C.; and the second pass, which produced high purity dicarboxylic acid as a heads cut, was at 290° C. Both passes were at 0.1 mm Hg. The results are listed in Table IV below.

TABLE IV

| | WFE Yields* | | | Dicarboxylic Acid** | | |
|---|---|---|---|---|---|---|
| | | Dicarboxylic | | | | Gardner |
| Run # | Heads | Acid | Bottoms | Purity | Acid # | Color |
| 1 | 59.4 | 32.9 | 6.8 | 94 | 306 | 3 |
| 2 | 59.4 | 32.9 | 6.8 | 94 | 306 | 3 |

*Yields are based on weight of each fraction obtained versus total weight of reaction mixture.
**Purity based on GC analysis with no correction for response factors. The rest of the material is unreacted fatty acid which was not removed on the first WFE pass.

Many modifications and variations of the present invention will be apparent to one of ordinary skill in the art in light of the above teaching. It is understood therefore that the scope of the invention is not to be limited by the foregoing description but rather is to be defined by the claims appended hereto.

What is claimed is:

1. A process for the production of a 21 carbon dicarboxylic acid capable of being distilled to a purity of at least 95% which comprises reacting a fatty acid mixture containing conjugated linoleic acid, in the absence of a catalyst, with up to 26% by weight of said fatty acids of acrylic acid at a temperature between 180° C. to 300° C. to convert the conjugated linoleic acid portion to said dicarboxylic acid having the formula:

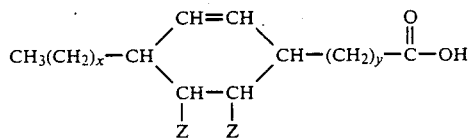

wherein X and Y are integers, X and Y together equal 12, at least one Z is a carboxylic acid group and any remaining Z is hydrogen.

2. The process of claim 1 wherein said fatty acid mixture is selected from the group consisting of tall oil fatty acid, soybean oil fatty acid, corn oil fatty acid, peanut oil fatty acid, linseed oil fatty acid, and cottonseed oil fatty acid.

3. The process of claim 1 wherein said temperature is between 230° C. and 260° C.

4. The process of claim 1 further comprising means for distilling the dicarboxylic acid-containing fatty acid mixture to recover a fraction containing at least 30% of the linoleic acid fraction as a dicarboxylic acid of at least 95% purity and a residual fraction.

5. The process of claim 4 further comprising means for distilling the dicarboxylic acid-containing fatty acid mixture to recover a fraction containing at least 50% of the linoleic acid fraction as a dicarboxylic acid of at least 95% purity and a residual fraction.

* * * * *

UNITED STATES PATENT AND TRADEMARK OFFICE
CERTIFICATE OF CORRECTION

PATENT NO. : 5,053,534
DATED : October 1, 1991
INVENTOR(S) : John P. Cosgrove

It is certified that error appears in the above—identified patent and that said Letters Patent is hereby corrected as shown below:

Column 3, line 25, delete "C-thermal"; and insert -- C-36 thermal --.

Signed and Sealed this

Seventh Day of June, 1994

Attest:

BRUCE LEHMAN

Attesting Officer     Commissioner of Patents and Trademarks